(12) United States Patent
Sutty et al.

(10) Patent No.: US 12,343,185 B2
(45) Date of Patent: Jul. 1, 2025

(54) DEVICE AND METHOD FOR SECURELY HOLDING BREAST ON MAMMOGRAPHY IMAGING SYSTEM

(71) Applicant: GE Precision Healthcare LLC, Wauwatosa, WI (US)

(72) Inventors: Jerome Sutty, Verrières le Buisson (FR); Thierry Bayle, Ponthévrard (FR); Sandrine Michelot, Voisins le Bretonneux (FR)

(73) Assignee: GE Precision Healthcare LLC, Wauwatosa, WI (US)

( * ) Notice: Subject to any disclaimer, the term of this patent is extended or adjusted under 35 U.S.C. 154(b) by 244 days.

(21) Appl. No.: 18/089,873

(22) Filed: Dec. 28, 2022

(65) Prior Publication Data

US 2024/0215934 A1  Jul. 4, 2024

(51) Int. Cl.
*A61B 6/04* (2006.01)
*A61B 6/50* (2024.01)

(52) U.S. Cl.
CPC .......... *A61B 6/0435* (2013.01); *A61B 6/0414* (2013.01); *A61B 6/502* (2013.01)

(58) Field of Classification Search
CPC .......... A61B 6/00; A61B 6/04; A61B 6/0407; A61B 6/0414; A61B 6/0435; A61B 6/40; A61B 6/42; A61B 6/4429; A61B 6/502; A61B 5/0071; A61B 5/0075; A61B 5/0091; A61B 5/708
See application file for complete search history.

(56) References Cited

U.S. PATENT DOCUMENTS 6,765,984 B2    7/2004  Higgins et al.
7,502,441 B2 *  3/2009  Lebovic ................. A61B 6/502
                                                    378/68

(Continued)

FOREIGN PATENT DOCUMENTS

JP    2011212111 A    10/2011
WO    2013074942 A1    5/2013

OTHER PUBLICATIONS

EP application 23214208.3 filed 05DEC2023—extended Search Report issued Apr. 26, 2024; 16 pages.

(Continued)

*Primary Examiner* — Jurie Yun
(74) *Attorney, Agent, or Firm* — Boyle Frederickson, S.C.

(57) ABSTRACT

According to one aspect of an exemplary embodiment of the disclosure, an imaging device or system, e.g., a mammography imaging system or device, includes a breast holding pad disposed on one or both of a compression paddle and a compression surface on the imaging device. The breast holding pad is formed with a central layer, a first, securing adhesive layer on one side of the central layer and a second, biocompatible adhesive layer disposed on the opposite side of the central layer. The biocompatible adhesive operates to securely hold the breast during any imaging and/or biopsy procedure performed utilizing the imaging system. Further, with the use of one or both pads, the amount of compression force required to hold the breast in a stationary position between the compression paddle and the compression surface can be reduced, thereby decreasing the discomfort to the patient during the imaging and/or biopsy procedure performed.

15 Claims, 4 Drawing Sheets

(56) References Cited

U.S. PATENT DOCUMENTS

| | | |
|---|---|---|
| 7,505,555 B2 | 3/2009 | Hermann et al. |
| 9,498,169 B1 | 11/2016 | Boutte et al. |
| 10,004,470 B2 | 6/2018 | Muller et al. |
| 2012/0033786 A1 | 2/2012 | Zinreich Shafer |
| 2020/0060632 A1 | 2/2020 | Blaski et al. |
| 2021/0022689 A1 | 1/2021 | Makino |

OTHER PUBLICATIONS

JP2011212111 Abstract, English Translation obtained from Espacenet Jul. 24, 2024; 1 page.

\* cited by examiner

DEVICE AND METHOD FOR SECURELY HOLDING BREAST ON MAMMOGRAPHY IMAGING SYSTEM

FIELD OF THE DISCLOSURE

The present disclosure relates generally to medical imaging systems, including mammography systems and devices, and more specifically to patient holding systems utilized with a medical imaging device.

BACKGROUND OF THE DISCLOSURE

Embodiments of the invention relate generally to X-ray medical imaging, and more particularly to devices, systems and methods employed to perform various imaging procedures, such as mammography imaging procedures including but not limited to spectral mammography (SM), such as 2D/3D dual-energy contrast-enhanced (CE) mammography exams, full-field digital mammography (FFDM) or digital breast tomosynthesis (DBT) mammography exams.

Spectral mammography (SM) is an X-ray imaging modality used to scan breasts for screening, diagnosis and/or interventional examinations. The effectiveness of spectral mammography is affected by numerous factors, one of which is the two-dimensional (2D) rendering of images obtained using SM.

Alternative systems to SM are also known for breast imaging. Some examples include full-field digital mammography, which captures the image directly onto a flat-panel detector, computed radiography, which involves the use of a cassette that contains an imaging plate), or digital breast tomosynthesis (DBT). A digital breast tomosynthesis (DBT) or mammography-tomography (mammo-tomo) system is a dedicated mammography system that acquires several (e.g., tens of) angularly offset projection X-ray images and uses the resulting X-ray image data to reconstruct three-dimensional (3D) image datasets.

The 3D image datasets are used to form various volumetric representations of the imaged breast, including an entire 3D volume of the breast, and various 3D sections of the 3D volume, such as slices or slabs constituting specified thicknesses of the 3D volume oriented to provide the desired view of one or more regions of interest (ROI) detected within the 3D image dataset.

In addition, when the 3D image datasets of the breast have been produced, after being utilized in a suitable diagnosis procedure, they can be utilized to guide a biopsy device employed with the DBT system into the breast to obtain a biopsy of the region of interest (ROI) identified within the 3D image datasets. In DBT systems, the biopsy device is disposed directly on the DBT system in order to be able to perform the biopsy utilizing the 3D image dataset to guide the biopsy device to the ROI.

With regard to the use of mammography devices, the process of obtaining high quality mammographic images from breast tissue requires a technician to position the breast of a patient between one or more paddles and/or support surfaces that compress the breast in order to immobilize and flatten it during image acquisition. The compression force applied to a breast improves image quality by reducing the thickness of the breast while spreading the breast tissue over a larger area, which facilitates interpretation of obtained imagery since the amount of overlying tissue for structures within the imaged breast is minimized.

Reduction of the breast thickness by compression is also important in managing patient radiation dosage. In general, the thicker the compressed breast, the more x-ray attenuation. Therefore, a higher x-ray dosage is necessary when imaging thicker breast tissue as compared to the dosage required for thinner tissue. While greater compression forces are desirable for obtaining clear images with lower radiation dosages, greater compression forces may contribute to patient pain or discomfort. Such patients may not schedule or may delay any future examinations due to the fear of an uncomfortable procedure, thereby possibly increasing the risk that a serious medical condition may not be detected in a timely fashion.

In many diagnostic mammography imaging devices, such that disclosed in US Patent Application Publication No. US20200060632, entitled Apparatus And Method For Mammographic Breast Compression, the entirety of which is expressly incorporated herein by reference for all purposes, the compression of the breast on the mammography imaging device is controlled by the technician using a footswitch with a binary positioning system, i.e., the footswitch is moveable between an "on" position to cause movement of the compression paddle(s) and an "off" position where the compression paddle(s) are stationary. When the footswitch is on the 'on' position, the paddle(s) is moved towards the breast under the full operational speed of the motor operably connected to the paddle(s) until contact of the paddle(s) with the breast is detected.

The contact between the paddle and the breast is detected in various manners, including the view of the technician seeing the paddle contacting and compressing the breast and/or through the use of various systems such as, for example, force sensors disposed on the paddle or other breast-contacting surface that measure the force applied to the breast to maintain the compression forces below certain predetermined thresholds. Depending on the patient, however, even compression forces below predetermined thresholds may cause pain or discomfort.

In addition, as the movement of the paddle towards the breast prior to contact with the breast is at a relatively high rate of speed, which can create unease in the patient upon viewing the fast movement of the paddle, on many occasions due to the delay in reaction by the technician controlling the movement of the paddle via the footswitch and/or the detection by force sensors of the contact of the paddle with the breast, the speed of the paddle upon contact with the breast can create compressive forces on the breast that exceed the predetermined threshold. Further, though the technician can attempt to avoid this by incrementally using the footswitch, the delay can still cause the paddle to contact the breast at a higher rate of speed than desired. Though this initial high compressive force on the breast is normally short in duration, as they are detected by the technician and/or force sensor shortly after initial contact of the paddle with the breast, with the speed of the paddle being quickly reduced or stopped, the initial contact can result in pain or discomfort to the patient.

Furthermore, either just prior to or after the paddle is moved into initial contact with the patient, the movement of the paddle is controlled in a finer manner by the technician to slowly achieve a desired compression force on the breast for optimal imaging of the breast. In performing this more closely controlled, finer movement of the paddle, the technician employs the footswitch to move the paddle, but by activating the footswitch in successive short intervals or periods of time to incrementally move the paddle towards the breast and reach the target compressive force to be exerted on the breast. In addition to, or alternatively to the footswitch, the mammography imaging device may include a fine movement adjustment knob. Rotation of the knob by the technician causes the paddle to move towards or away from the breast in a finer manner than the footswitch to more accurately position the paddle against the breast to achieve the desired compressive force on the breast.

However, even though the technician can closely control the movement of the paddle to contact the breast with the desired compressive force and attempt to minimize any unnecessary pain or discomfort to the patient, the balance between sufficiently compressing the breast and minimizing patient discomfort can result in situations where the breast moves between the paddle(s) and/or breast-contacting support surfaces during the imaging or biopsy procedure. This result is highly undesirable as it requires repositioning and recompression of the breast to perform a subsequent imaging and/or biopsy procedure.

In addition to the adjustment of the position of the paddle(s) and/or other breast-support surface(s), to accommodate and minimize discomfort from compression of the breast, other devices have been developed that are attached to the imaging device or system. In particular, U.S. Pat. Nos. 6,765,984 and 7,505,555, the entirety of which are each expressly incorporated herein by reference for all purposes, disclose a radiolucent cushion or pad that is attached to a breast support surface. In certain embodiments of the pad, the pad can be formed with an adhesive on one side of the pad, such as a double sided adhesive tape, to adhere the tape to the pad and to a backing member attached to the support surface or directly to the support surface in order to hold the pad on the compression surface. Alternatively, the '555 patent discloses that various coatings, layers or other materials can be applied to the material forming the pad, such as a gel, in order to provide the adherence to the paddle or compression/support surface. The material forming the pad itself, such as the gel, may also have any inherent tacky surface that is able to hold the pad on the compression surface.

However, as also disclosed in the '555 patent, the tacky surface is undesirable for patient contact. As such, while the pad provides an enhancement to the comfort for the breast of the patient, the pad does not provide any enhancement to the ability of the paddle and or compression surfaces including the pad to hold the breast in position on the mammography device.

Therefore, with regard to the aforementioned shortcomings of prior art imaging systems concerning the ability of those imaging systems to adequately hold the compressed breast in position during imaging and biopsy procedures, it is desirable to develop an improved device, system and method for the maintaining the position of the breast during the operation of the of the imaging system and/or biopsy system.

SUMMARY OF THE DISCLOSURE

According to one aspect of an exemplary embodiment of the present disclosure, a breast holding pad for a mammography imaging system includes a central layer and a biocompatible adhesive layer disposed on one side of the central layer.

According to still another aspect of an exemplary embodiment of the present disclosure, a mammography system includes a gantry including radiation source, a detector alignable with the radiation source and defining a compression surface, and a compression paddle moveable relative to the compression surface to secure a patient breast therebetween, a controller operably connected to the gantry to control the operation and movement of the compression paddle, radiation source and detector to generate image data, the controller including a central processing unit and interconnected database for processing the image data from the detector, a display operably connected to the controller for presenting information to a user, and a user interface operably connected to the controller to enable user input to the controller, and at least one breast holding pad disposed on the gantry to hold the compressed the breast on the gantry, wherein the at least one breast holding pad is formed of a central layer, and a biocompatible adhesive layer disposed on one side of the central layer.

According to still another aspect of an exemplary embodiment of the present disclosure, a method for holding an object to be imaged on an imaging system includes the steps of providing an imaging system including a gantry disposed movably disposed on a support surface and including a radiation source, a detector alignable with the radiation source, the detector having a compression surface on which an object to be imaged is adapted to be positioned, and a compression paddle moveable relative to the compression surface to secure the object therebetween, a controller operably connected to the gantry to control the operation and movement of the compression paddle, the radiation source and detector to generate image data in an imaging procedure performed by the imaging system, the controller including a central processing unit and interconnected database for processing the image data from the detector to create images, a display operably connected to the controller for presenting information to a user, and a user interface operably connected to the controller to enable user input to the controller, positioning at least one object holding pad on the gantry, the at least one object holding pad including a central layer and a biocompatible adhesive layer disposed on one side of the central layer, positioning the object on the compression surface between the radiation source and the detector, and operating the compression paddle to compress the object between the compression paddle and the compression surface to engage the object with the at least one object holding pad.

These and other exemplary aspects, features and advantages of the invention will be made apparent from the following detailed description taken together with the drawing figures.

BRIEF DESCRIPTION OF THE DRAWINGS

The drawings illustrate the best mode currently contemplated of practicing the present invention.

In the Drawings.

DETAILED DESCRIPTION OF THE DRAWINGS

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

As used herein, "electrically coupled", "electrically connected", and "electrical communication" mean that the referenced elements are directly or indirectly connected such that an electrical current may flow from one to the other. The connection may include a direct conductive connection, i.e., without an intervening capacitive, inductive or active element, an inductive connection, a capacitive connection, and/or any other suitable electrical connection. Intervening components may be present.

Further, while the embodiments disclosed herein are described with respect to a mammography apparatus for the 2-dimensional imaging of breast tissue, it is to be understood that embodiments of the invention may be applicable to other types of imaging devices for both 2-dimensional and 3-dimensional imaging including, for example, fluoroscopy, full-filed digital mammography, digital breast tomosynthesis (DBT) and spectral mammography (single or multi-energy), as well as for imaging procedures for tissue other than breast tissue. Further still, embodiments of the invention may be used to analyze tissue, generally, and are not limited to analyzing human tissue.

Figure 1:
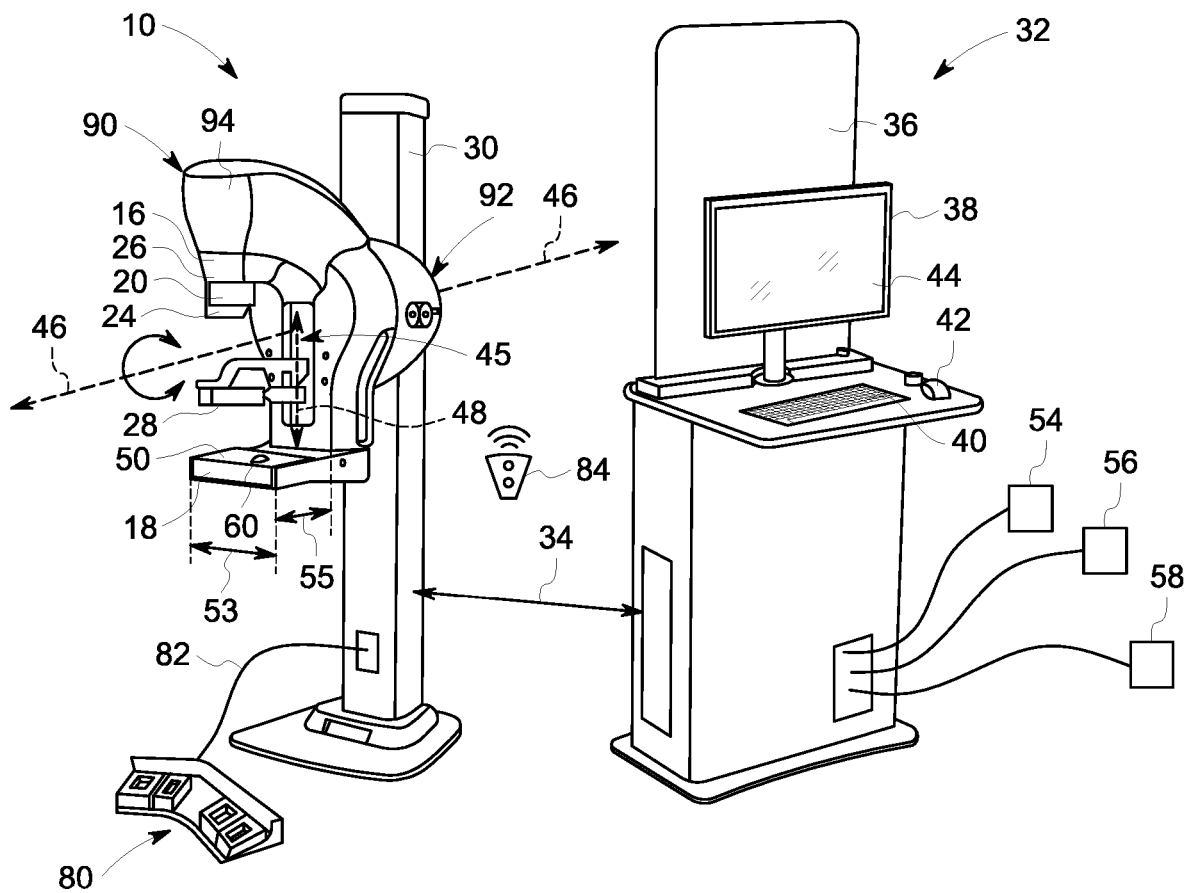
FIG. 1 is a perspective view of an imaging device in the form of a mammography apparatus for imaging the breast tissue of a patient, in accordance with an embodiment of the disclosure.
Figure 2:
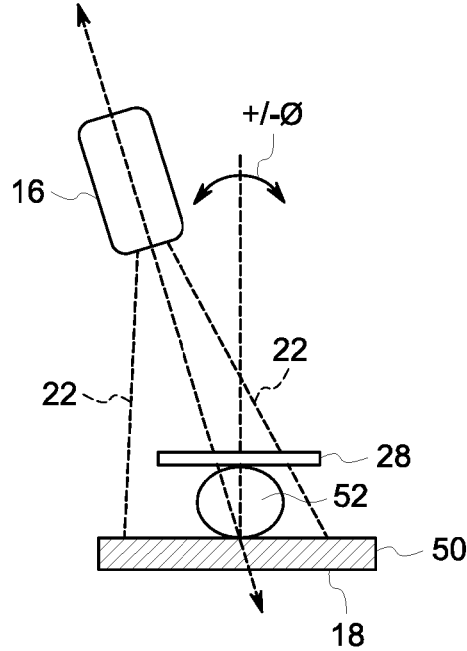
FIG. 2 is a diagram of the system of FIG. 1, showing the radiation source of the system in a scanning position, in accordance with an embodiment of the disclosure.
Figure 3:
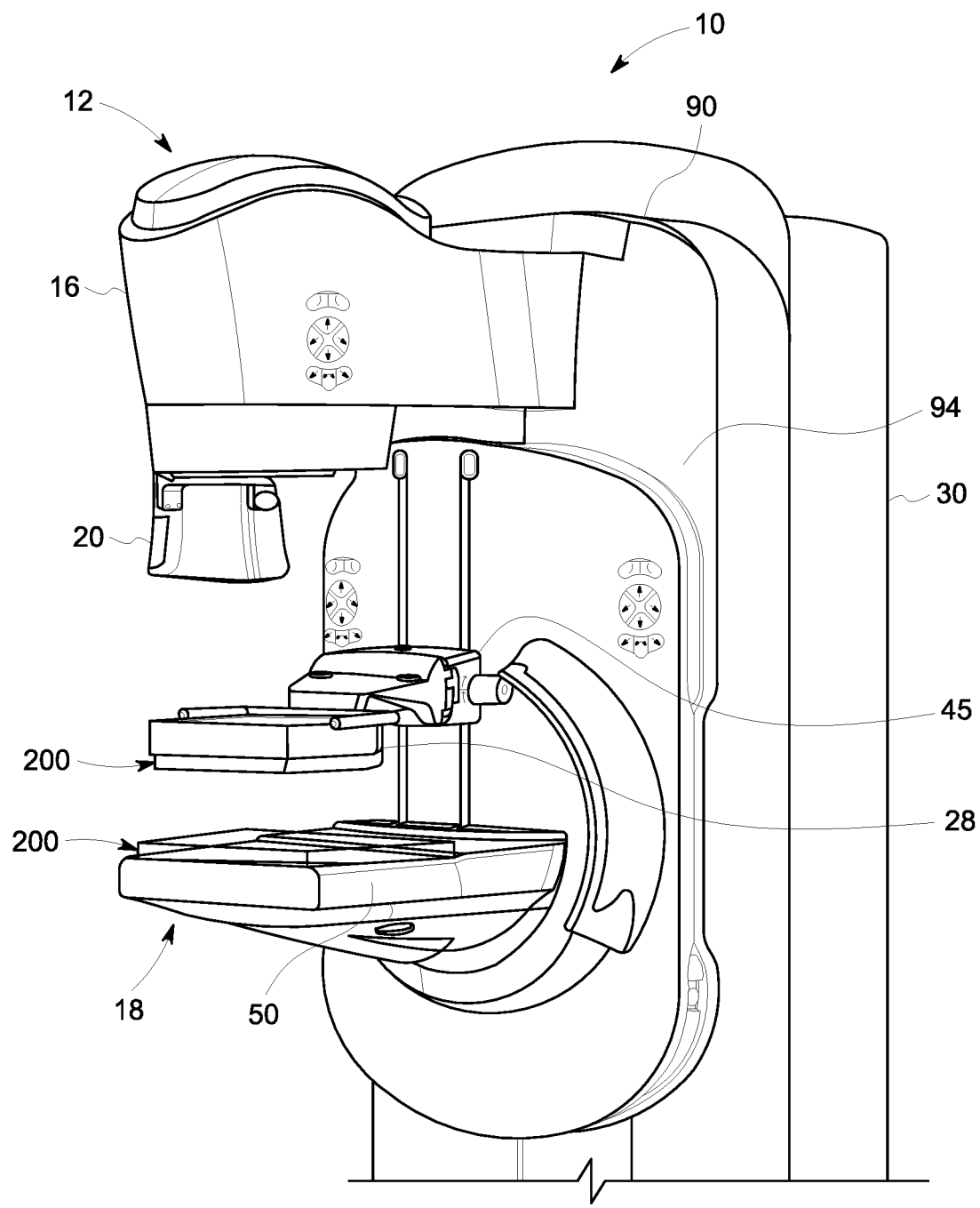
FIG. 3 is a isometric view of the mammography system of FIG. 1 including a first embodiment of a breast holding pad thereon in accordance with an embodiment of the disclosure.

Referring now to FIGS. 1 and 2, the major components of an exemplary imaging system 10 formed as a mammography system 12 for imaging breast tissue according to an embodiment of the invention are shown. The system 10, such that disclosed in US Patent Application Publication No. US20200060632, entitled Apparatus And Method For Mammographic Breast Compression, the entirety of which is expressly incorporated herein by reference for all purposes, includes a radiation source/x-ray source 16, a radiation detector 18, and a collimator 20. The radiation source 16 is movable between a variety of imaging positions relative to the detector 18, and is operative to emit radiation rays 22 (FIG. 2) that are received by the radiation detector 18 to provide an image of an object, such as a breast 52. In embodiments, the system 10 may include a patient shield 24 mounted to the radiation source 16 via face shield rails 26 to prevent the patient's head from obstructing the radiation rays and protecting the patient from the radiation rays 22.

Referring still further to FIGS. 1 and 2, the system 10 also includes a compression paddle or plate 28 and a support structure 30 to which one or more of the radiation source 16, radiation detector 18, and/or compression plate 28 may be mounted to. In embodiments, the system 10 may further include a controller 32. The controller 32 may be a workstation having at least one processor/central processing unit/computer and a memory device/database that stores information and/or instructions for the operation of the system 10 that are employed by the controller 32, as shown in FIG. 1 or, in other embodiments, the controller 32 may be embedded/integrated into one or more of the various components of the system 10 disclosed above. In embodiments, the controller 32 may be in electrical communication with the radiation source 16, radiation detector 18, and/or the compression plate 28 via a cable 34. As will be appreciated, in embodiments, the connection 34 may be a wireless connection. In embodiments, the controller 32 may include a radiation shield 36 that protects an operator of the system 10 from the radiation rays 22 emitted by the radiation source 16. The controller 32 may further include a display 38, a keyboard 40, mouse 42, and/or other appropriate user input devices that facilitate control of the system 10 via a user interface 44.

As further shown in FIGS. 1 and 2, the radiation source 16, along with the radiation detector 18, forms part of an x-ray system which provides x-ray imagery for the purpose of imaging a body part of a patient, such as breast 52. As stated above, the radiation source 16 emits the radiation rays 22 such that the radiation rays 22 travel from the radiation source 16 to the radiation detector 18. While the radiation rays 22 are discussed herein as being x-rays, it is to be understood that the radiation source 16 may emit other types of electromagnetic rays which can be used to image a patient. The radiation source 16 may be mounted to the support structure 30 such that the radiation source can rotate around an axis 46 in relation to the radiation detector 18, although movement of the radiation source 16 in paths other than rotation about a fixed axis, such as during digital breast tomosynthesis (DBT), are also envisioned. In embodiments, the radiation detector 18 may be configured to rotate or translate within its housing, such as in the directions indicated by arrows 53 and 55.

In the illustrated exemplary embodiment of FIG. 1 the radiation source 16 and the detector 18 are mounted to a gantry 90 that is secured to the support structure 30. The support structure 30 houses a translation mechanism 92 that is operably connected to the gantry 90. The translation mechanism 92 is operable to move the gantry 90 vertically with respect to the support structure 30 in order to position the gantry 90 at the appropriate height to accommodate the dimensions of the patient on which the system 10 is being utilized. The translation mechanism 92 is also operable to rotate the gantry 90 relative to the support structure 30 about the horizontal axis 46 in order to position the gantry 90 rotationally with regard to the patient, as necessary.

The gantry 90 includes a generally C-shaped body 94 with the radiation source 16 at one end and the detector 18 at the opposite end. In this configuration, regardless of the vertical and/or rotational orientation of the gantry 90, such as to position the radiation source 16 and detector 18 relative to the patient breast 52 to obtain x-ray images at various orientations, such as for craniocaudal (CC) or mediolateral oblique (MLO) views, among others, the radiation source 16 is disposed in alignment with the detector 18. In this position, the detector 18 is capable of receiving the x-rays 22 emitted from the radiation source 16 that pass through the portion of the patient, i.e., patient breast 52, located between the radiation source 16 and the detector 18 in order to generate image data for transmission to the control system 32 of the mammography device/system 10 to create/reconstruct a 3D image dataset for viewing by a physician, such as by using DBT, among other known methods.

Additionally, in another embodiment the radiation source 16 can be attached to the gantry 90 to rotate and/or move independently of the gantry 90 and detector 18 in order to enable the radiation source 16 to take x-ray images of the patient breast at various angles relative to the detector 18, e.g., between +/−60°. The images obtained between these angles for the radiation source 16 can be used either for creation of stereoscopic images in a biopsy procedure using the system 10 or for DBT when operating the system 10 in an imaging mode.

As stated above, the radiation detector 18 receives the radiation rays 22 emitted by the radiation source 16. In embodiments, data regarding the radiation rays 22 received by the radiation detector 18 may be electrically communicated to the controller 32 from the radiation detector 18 via cable/electronic connection 34 such that the controller 32 generates one or more images which may be shown on the display 38 and stored in the memory device.

The compression plate 28 is operative, in response to instruction from the controller 32 or in response to instructions from controller(s) on or near the mammography system 10 or switch controllers 80, to move towards and away from the radiation detector 18 as indicated by arrows/compression axis 48 such that the compression plate 28 flattens and holds a body part, e.g., breast 52, in place against the surface 50 of the radiation detector 18. In this respect, the radiation detector 18 and the surface 50 thereof is referred to herein as a "compression surface or support plate" that cooperates with the compression plate 28 to compress and clamp a breast of a patient therebetween.

In one exemplary embodiment, in order to maintain the position of the patient breast 52 stationary during the imaging and/or biopsy procedures, the compression plate 28 is attached to a plate or paddle support mechanism 45 located on and/or within the gantry 90 that positions the compression plate 28 directly over and in alignment with the detector 18/support plate and operably connected to the controller 32. The plate support mechanism 45 is operable within the gantry 90 at any rotational or vertical position of the gantry 90 to move the plate 28 in a line either towards or away from the detector 18/support plate. The mechanism 45 can have any of a number of different configurations, but in one exemplary embodiment takes the form of a compression screw mechanism that is operable to move the plate 28 into engagement with the patient breast 52 to exert a predetermined pressure/compression on the breast 52 to retain the breast 52 in a stationary position between the plate 28 and the detector 18/support plate during imaging and/or biopsy procedures.

In operation, in accordance with an embodiment, the breast 52 of the patient may be placed onto the compression surface 50 of the radiation detector 18. The compression plate 28, under control of the plate support mechanism 45 by the controller 32, moves towards the detector 18 to compress the breast 52 against the surface 50 of the detector 18 such that the breast 52 is immobilized. Movement of the compression plate 28 towards the detector 18 to compress the breast 52 against the support plate/detector 18 defines a compression phase of the system 10. Once a target compression is achieved, movement of the compression plate 28 is halted and the compression plate 28 and the support plate 18 are held in fixed position to clamp the breast 52 therebetween (referred to herein as the clamping phase) so that imaging or procedures, e.g., a biopsy, may be commenced. During an imaging procedure, the radiation source 16 is selectively adjusted such that it is moved/rotated to a first scanning position and scans the breast 52. The radiation detector 18 receives the radiation rays 22 passing through the breast 52 and sends data to the controller 32 which then generates one or more x-ray images of the breast 52. Once imaging is complete, the controller 32 moves the compression plate 28 away from the support plate 18 to free the breast 52.

Referring still further to FIG. 1, in an embodiment, the system 10 may include one or more physiological monitoring or sensor devices 54, 56, 58, 60 communicatively coupled with the controller 32 for monitoring one or more physiological parameters of a patient (and for transmitting physiological parameter data to the controller 32). While FIG. 1 illustrates that the sensor devices 54, 56, 58 are connected to the controller 32, in some embodiments, one or more of the sensor devices may be communicatively coupled with the mammography apparatus, without departing from the broader aspects of the invention. The sensor devices may be selected to monitor and/or measure any physiological information of a patient desired, including, but not limited to, diastolic blood pressure, systolic blood pressure, body temperature, blood oxygen level, patient weight, skin conductance, pulse rate, etc. As illustrated in FIG. 1, one or more of the sensor devices, e.g., sensor device 60, may be physically integrated with the compression plate 28 and/or the detector/support plate 18. By incorporating the sensor devices into the support plate 18 or compression plate 28, physiological parameter data of the patient may be acquired and transmitted to the controller 32 without requiring any additional intervention by the system operator.

In an embodiment, the sensor device 60 may be a force sensor for measuring the amount of pressure or compressive force applied to the breast 52. Additional sensors for measuring physiological parameters may be configured to either directly measure or allow the calculation of variables such as force, pressure, temperature, rigidity, elasticity, breast size and/or volume, and/or tissue density and could be embedded in compression plate 28 or support plate 18 or attached as part of mammography system 10.

Referring once again to FIG. 1, in an embodiment, operation of the system 10 during the compression phase and the clamping phase may be controlled by the patient using switch controls 80, e.g., footswitch controls, such as disclosed in U.S. Pat. No. 10,004,470, which is hereby incorporated by reference herein in its entirety. Switch controls 80 are typically connected via a cable/wire 82 to mammography imaging system 10. The controls are also often mirrored on the opposite side of mammography imaging system 10 (not shown). Other controls (not shown) may be present on particular accessories placed either in the paddle/breast support area. In an embodiment, rather than being footswitch controls, the switch controls may be a handheld control unit 84 with a wired, wireless, Bluetooth or other connection with the system 10. In an embodiment, the patient may control the rate of compression and/or pressure or force applied during the compression phase and/or clamping phase using the switch controls. A feedback device, e.g. controller 32, may be configured to give feedback information about the image to obtain and may designed such that the feedback information is operatively perceivable by the patient (e.g., through an audible or visual indication). The feedback device, e.g., controller 32, may be configured to provide feedback information to the patient regarding the rate of compression (greater or lower rate of compression) and/or amount of pressure (higher or lower) required to produce an optimal image, in dependence upon the information received from the various sensor devices 54, 56, 58, 60. In this respect, the feedback device informs the patient when compression rate and/or pressure applied is sufficient to obtain a quality image, as determined from a blood pressure or other measurement taken from the patient through sensing devices 54, 56, 58, or 60, before or during the compression and/or clamping phase.

Figure 4:
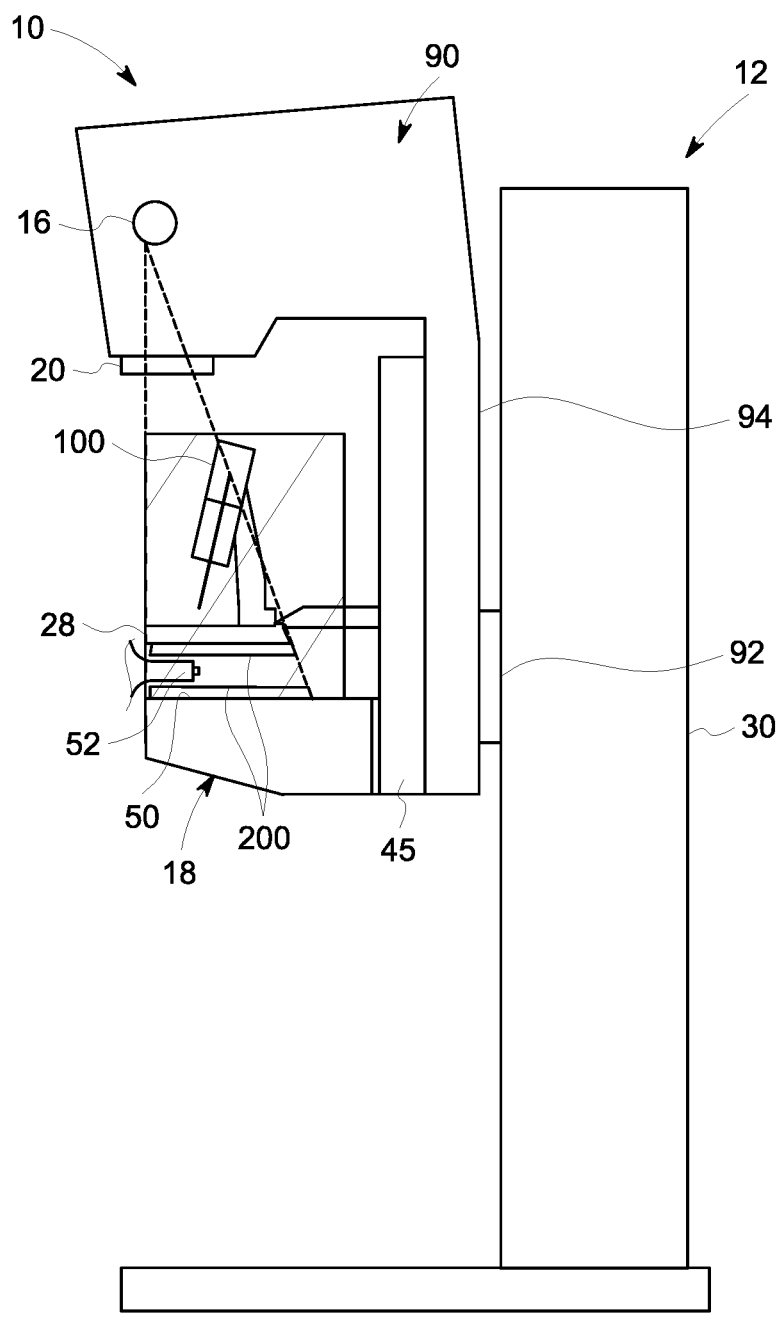
FIG. 4 is an isometric view of another embodiment of the mammography system and breast holding pad of FIG. 3 including a biopsy device, in accordance with an embodiment of the disclosure.

Referring now to FIG. 4, the imaging system 10 may further, or alternatively, include a biopsy system 100, such as that disclosed in which may be selectively removable from the imaging system 10. In such an embodiment, the radiation source 16, along with the radiation detector 18, forms part of an x-ray system which provides x-ray imagery for the purpose of guiding the biopsy tool 100 to a suspect site within a body part of a patient. As shown in FIG. 4, in embodiments, the biopsy system 100, may be disposed on the support structure 30 such that it also rotates about the axis 46, in a manner similar to the radiation source 16, and/or moves in a vertical and/or horizontal direction, in a manner similar to the compression plate 28.

Looking now at the exemplary illustrated embodiments of FIGS. 3-7, the mammography imaging system 10, with or without the biopsy system 100, includes a breast holding pad 200 on at least one of the compression plate 28 and the compression surface 50. The breast holding pad 200 operates to frictionally grip the breast 52 between the compression paddle 28 and the compression surface 50 in order to securely hold the breast 52 therebetween during any imaging and/or biopsy procedure performed utilizing the imaging system 10. Further, with the use of one or both pads 200, the amount of compression force required to hold the breast 52 in a stationary position between the paddle 28 and the compression surface 50 can be reduced, thereby decreasing the discomfort to the patient during the imaging and/or biopsy procedure performed using the mammography imaging system 10.

Figure 5:
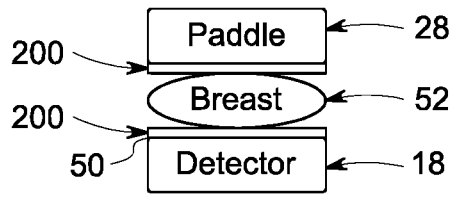
FIG. 5 is a schematic, cross-sectional view of the mammography system and breast holding pad of FIG. 3 compressing a breast.
Figure 6:
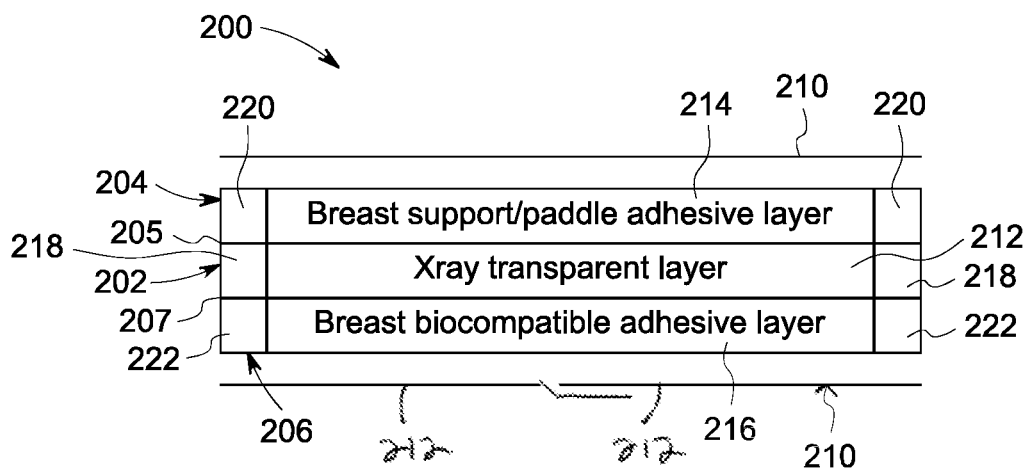
FIG. 6 is a schematic, cross-sectional view of the breast holding pad along line 6-6 of FIG. 5.

In the embodiment shown in FIGS. 4-6, the breast holding pad 200 is formed with a central layer 202, a first, securing or adhesive layer 204 on one side 205 of the central layer 202 and a second, biocompatible securing or adhesive layer 206 disposed on the opposite side 207 of the central layer 202 from the first adhesive layer 204. The first and second adhesive layers 204, 206 can each be covered by a release liner(s) 210 that protect the first and second adhesive layers 204, 206 prior to use of the pad 200 and are readily removable from the first and second adhesive layers 204, 206 when the pad 200 is ready for use on one of the paddle 28 or the compression surface 50. The release liner(s) 210 can be formed from multiple components 212 (FIG. 6) attached to opposed sides of one or both of the first and second securing or adhesive layers 204, 206, and disposed in an overlapping configuration, where one of the components 212 can be removed to enable one side of the first or second securing layer 204, 206 to be affixed to the compression surface 50. After affixing or securing the exposed end, the second component 212 can be removed to secure the opposite side of the first or second securing layer 204, 206 to the compression surface 50.

The central layer 202 is formed of an x-ray transparent or radiolucent material, such as those disclosed in U.S. Pat. Nos. 6,765,984 and 7,505,555, the entirety of which are each expressly incorporated herein by reference for all purposes. The central layer 202 can be formed of a compressible material, such as a foam or gel material, that functions as a cushion for the breast 52 in addition to acting to securely hold the breast 52 in the manner to be described. The central layer 202 can have any desired shape and/or configuration, and in the illustrated exemplary embodiment the pads 200 are each shaped to be complementary to the shape of the paddle 28 and the compression surface 50, respectively. In an alternative embodiment, the central layer 202 can be formed as a thin carrier layer, with the first adhesive layer 204 and the second adhesive layer 206 applied to either side in the form of a dual sided tape. In one exemplary embodiment, the pad 200 has a thickness of less than 1.0 mm, and in another exemplary embodiment less than 0.50 mm, and in still a further exemplary embodiment, a thickness of less than 0.25 mm.

The first adhesive layer 204 applied on one side 205 of the central layer 202 is utilized to secure the pad 200/central layer 202 to the paddle 28 or to the compression surface 50. Further, the first adhesive layer 204 is selected to be at least partially formed from an adhesive that is x-ray transparent or radiolucent and that securely holds the pad 200 on the paddle 28 or compression surface 50, while also leaving no residue on the paddle 28 or compression surface 50 when the pad 200 is removed. In an alternative embodiment, the first adhesive layer 204 can be omitted where the central layer 202 is attached to the paddle 28 or compression surface 50 in an alternative manner, such as by a mechanical securement, or where the central layer 202 is formed of a material having an inherent adhesive capability that can secure the central layer 202 directly to the paddle 28 or compression surface 50.

Opposite the first adhesive layer 204, the second adhesive layer 206 is applied to the other side 207 of the central layer 202 and utilized to engage and frictionally hold the breast 52 in a stationary position with regard to the pad 200. The second adhesive layer 206 can optionally be the same or different than the first adhesive layer 204, and optionally can be formed from a tacky but non-adhesive material, such as a silicon or silicon rubber material, and is selected to be at least partially a material or an adhesive that is x-ray transparent or radiolucent and that is biocompatible with the breast 52 to securely frictionally hold the breast 52 on the pad 200 in the compressed position, while also leaving no residue on the breast 52 when the compression applied to the breast 52 via the pad 200 is removed. The second adhesive layer 206 can be formed to cover the entire side of the central layer 202 or one or more portions thereof, in order to provide secure engagement of the second adhesive layer 206 with the breast 52. Further, the second adhesive layer 206 can be formed of a high friction material that is applied to the entire side 207 or on selected portions of the side 207, such as silicone rubber material.

Figure 7:
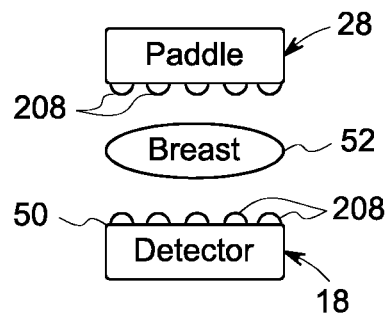
FIG. 7 is a schematic, cross-sectional view of the mammography system and a second embodiment of a breast holding pad thereon in accordance with an embodiment of the disclosure.

In an alternative embodiment, as shown in FIG. 7 the pad 200 can be formed of a single layer 208 of a material that can be used to from the second adhesive layer 206, but that is applied directly to one or both of the paddle 28 and the compression surface 50. In one embodiment, the single layer 208 can be formed of a high friction, biocompatible material, such as a silicone rubber, that is applied in a suitable pattern on the paddle 28 and/or compression surface 50, such as a grid or a concentric circular pattern, among others, in order to hold the breast 52 securely in position with regard to the paddle 28 and compression surface 50.

In addition, while prior exemplary embodiments have disclosed that the central layer 202, the securing adhesive 204 and the biocompatible adhesive 206 forming the pad 200 are each x-ray transparent, in alternative embodiments various portions of one or more of the central layer 202, the securing adhesive 204 and the biocompatible adhesive 206 can be formed of non-x-ray translucent materials, as these portions of the central layer 202, the securing adhesive 204 and the biocompatible adhesive 206 are disposed outside of the field of view of the imaging system 10. For example, the securing adhesive 204 can be disposed on the central layer 202 in a pattern that lies at least partially outside of the field of view, e.g., around the perimeter of the central layer 202, such that the securing adhesive 204 is not required to be x-ray transparent. Further, the central layer 202, the securing adhesive layer 204 and/or the biocompatible adhesive layer 206 can each include portions 212, 214, 216 within the field of view that are x-ray transparent and portions 218, 220, 222 outside of the field of view that are non-x-ray transparent. In addition, in another exemplary embodiment, for use in conjunction with a biopsy device or system 100, the pad 200, and in particular the various layers constituting the pad 200, can include one or more apertures (not shown) therein optionally in alignment with suitable openings (not shown) present in the paddle 28, which allow for the biopsy needle to extend through the pad 200 into the breast 52 to perform the biopsy procedure without engaging any portion of the pad 200. Thus, the pad 200 can securely hold the breast 52 in the desired position relative to the paddle 28, the compression surface 50 and the biopsy system 100 without interfering with the performance of the biopsy procedure.

With regard to another exemplary embodiment of the disclosure, the pad 200 can be formed with a central layer/carrier 202 formed of plastic material, such as thermoplastic elastomer, including a polypropylene film, among others, and the first adhesive layer 204 and the second adhesive layer 206 each formed of a silicone adhesive or an acrylic adhesive, among others. Further the release liner can be formed from a coated (silicon or fluoro-silicon coated) or uncoated material, such as a polypropylene, a polyester or a paper, e.g., kraft paper, material.

It is understood that the aforementioned compositions, apparatuses and methods of this disclosure are not limited to the particular embodiments and methodology, as these may vary. It is also understood that the terminology used herein is for the purpose of describing particular exemplary embodiments only, and is not intended to limit the scope of the present disclosure which will be limited only by the appended claims.

We claim:

1. A breast holding pad for a mammography imaging system, the pad comprising:
   a. a central layer;
   b. a biocompatible adhesive layer disposed on one side of the central layer; and
   c. a securing adhesive layer disposed on the central layer opposite the side of the central layer on which the biocompatible adhesive layer is disposed.

2. The breast holding pad of claim 1, wherein the biocompatible adhesive layer is integrally formed with the central layer.

3. The breast holding pad of claim 1, wherein the central layer is formed at least partially of an x-ray transparent material.

4. The breast holding pad of claim 3, wherein the central layer is formed of a foam material.

5. The breast holding pad of claim 1, wherein the central layer is formed of a carrier material.

6. The breast holding pad of claim 1, wherein the biocompatible adhesive layer and the securing adhesive layer are different from one another.

7. A mammography system comprising:
   a. a gantry including a radiation source, a detector alignable with the radiation source and defining a compression surface, and a compression paddle moveable relative to the compression surface to secure a patient breast therebetween;
   b. a controller operably connected to the gantry to control the operation and movement of the compression paddle, radiation source and detector to generate image data, the controller including a central processing unit and an interconnected database for processing the image data from the detector, a display operably connected to the controller for presenting information to a user, and a user interface operably connected to the controller to enable user input to the controller; and
   c. at least one breast holding pad disposed on the gantry to hold the compressed breast on the gantry, wherein the at least one breast holding pad is formed of:
      i. a central layer;
      ii. a biocompatible adhesive layer disposed on one side of the central layer; and
      iii. a securing adhesive layer disposed on the central layer opposite the side of the central layer on which the biocompatible adhesive layer is disposed,
   wherein the biocompatible adhesive layer and the securing adhesive layer are different from one another.

8. The mammography system of claim 7, wherein the at least one breast holding pad is disposed on at least one of the compression paddle, and the compression surface.

9. The mammography system of claim 8, wherein the biocompatible adhesive layer is integrally formed with the central layer.

10. The mammography system of claim 7, wherein the central layer is formed at least partially of an x-ray transparent material.

11. The mammography system of claim 7, wherein the central layer is formed of a foam material.

12. The mammography system of claim 7, wherein the central layer is formed of a carrier material.

13. A method for holding an object to be imaged on an imaging system, the method comprising the steps of:
   a. providing an imaging system comprising:
      i. a gantry disposed movably disposed on a support surface and including a radiation source, a detector alignable with the radiation source, the detector having a compression surface on which an object to be imaged is adapted to be positioned, and a compression paddle moveable relative to the compression surface to secure the object therebetween;
      ii. a controller operably connected to the gantry to control the operation and movement of the compression paddle, the radiation source and detector to generate image data in an imaging procedure performed by the imaging system, the controller including a central processing unit and an interconnected database for processing the image data from the detector to create images, a display operably connected to the controller for presenting information to a user, and a user interface operably connected to the controller to enable user input to the controller;
b. positioning at least one object holding pad on the gantry, the at least one object holding pad including a central layer, and a biocompatible adhesive layer disposed on one side of the central layer and a securing adhesive layer disposed on the central layer opposite the side of the central layer on which the biocompatible adhesive layer is disposed;
c. positioning the object on the compression surface between the radiation source and the detector; and
d. operating the compression paddle to compress the object between the compression paddle and the compression surface to engage the object with the at least one object holding pad, wherein the step of positioning at least one object holding pad on the gantry comprises positioning the securing adhesive layer against the compression paddle, the compression surface, or combinations thereof.

14. The method of claim 13, wherein the step of operating the compression paddle to compress the object between the compression paddle and the compression surface to engage the object with the at least one object holding pad reduces the compressive force required to securely hold the object between the compression paddle and the compression surface.

15. The method of claim 13, further comprising the steps of:
a. operating the radiation source and detector to generate image data in an imaging procedure;
b. operating the compression paddle to decompress the object between the compression paddle and the compression surface and disengage the object from the at least one object holding pad; and
c. removing the at least one object holding pad from the gantry.

* * * * *